(12) United States Patent
Westbrook et al.

(10) Patent No.: US 6,743,799 B2
(45) Date of Patent: *Jun. 1, 2004

(54) USE OF PDE V INHIBITORS FOR IMPROVED FECUNDITY IN MAMMALS

(75) Inventors: Simon Lempriere Westbrook, County of Kent (GB); Johannes Fridrich Zanzinger, County of Kent (GB)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 10/229,534

(22) Filed: Aug. 27, 2002

(65) Prior Publication Data

US 2003/0018037 A1 Jan. 23, 2003

Related U.S. Application Data

(63) Continuation of application No. 09/982,445, filed on Oct. 18, 2001, now Pat. No. 6,548,508.
(60) Provisional application No. 60/253,338, filed on Nov. 28, 2000.

(30) Foreign Application Priority Data

Oct. 20, 2000 (GB) .............................................. 0025782

(51) Int. Cl.[7] ........................................... A61K 31/519
(52) U.S. Cl. ................................................ 514/258.1
(58) Field of Search ....................................... 514/258.1

(56) References Cited

U.S. PATENT DOCUMENTS 6,548,508 B2 * 4/2003 Westbrook et al. ...... 514/258.1

FOREIGN PATENT DOCUMENTS

| WO | WO 94/28902 | * 12/1994 |
| WO | WO 00/51973 | 9/2000 |

OTHER PUBLICATIONS

Cuadra, Deborah et al., "Type 5 phosphodiesterase regulation of human sperm motility," *Am J Obstet* Gynecol, vol. 182, No. 5, 1013–1015 (2000).
Friedman, et al, "Sildenafil Citrate (Viagra) Increases Uterine Blood Flow and Potentiates Estrogen–Induced Vasodilation," *J. Soc Gynecol Investig*, vol. 8, No. 1, 814 (2001).
"Viagra treatment for female infertility," *Database Phind 'Online!*, Access. No. 00662558, 30 (2000).
Zoma, "Poster Session: Reproductive Endocrinology II," No. 814 (2001).
"Drug Actions—Basic principles and Therapeutic Aspects," 77 (1995).
Hanson et al., Medline Abstract, *Am J Physiology*, Pediatr. Res 43(2), 163–8 (1998).
Sanchez et al., Medline Abstract, *Pediatr. Res.*, 43(2), 163–8 (1998).
Defouw et al., *Endothelium*, 7(3), 193–200 (2000).
Thebaud et al., *Intensive Care Medicine*, 25(3), 300–3 (1999).
Ziegler et al., *Am J Resp. and Critical Care Medicine*, vol. 157, No. 4, Part 1, 1104–1110 (1998).
WE Paulus et al., Human Reproduction (Oxford) vol. 16, abstract book No. 1, 2001 pp. 116–117, 17[th]Annual Meeting of the European Society of Human Rproduction and Embryology, Lausanne, Switzerland, Jul. 1st–14th 2001.

* cited by examiner

Primary Examiner—Raymond J. Henley, III
(74) Attorney, Agent, or Firm—Lorraine B. Ling; Kohn & Associates, PLLC; Kenneth I. Kohn

(57) ABSTRACT

The invention relates to the use of a cyclic guanosine 3',5'-monophosphate phosphodiesterase type five (cGMP PDE V) inhibitor for increasing fecundity in a mammal by one or more of (a) promoting the growth of an oocyte, zygote, blastocyst, embryo and/or foetus, (b) increasing the rate or probability of survival of an embryo and/or foetus and (c) increasing the birth weight of a progeny, or for increasing milk productivity.

2 Claims, 4 Drawing Sheets

USE OF PDE V INHIBITORS FOR IMPROVED FECUNDITY IN MAMMALS

CROSS REFERENCE TO RELATED APPLICATIONS

This is a continuation application of U.S. Ser. No. 09/982,445, filed Oct. 18, 2001, now U.S. Pat. No. 6,548,508 which claims benefit of priority from U.S. Provisional Application No. 60/253,338, filed Nov. 28, 2000 and from United Kingdom Application No. 0025782.4, filed Oct. 20, 2000.

FIELD OF THE INVENTION

This invention relates to a new use of certain substances in mammals. More specifically, it relates to the use of cyclic guanosine 3', 5'-monophosphate phosphodiesterase type five (cGMP PDE V) inhibitors to increase fecundity in mammals.

BACKGROUND ART

There is a constant need, in the husbandry of food animals, to increase economic efficiency. One way of achieving this is by increasing the efficiency of the breeding process by, for instance, increasing the chances of a viable pregnancy occurring, increasing the number of offspring per pregnancy and reducing the mortality of young animals. The mortality rate of young animals, particularly piglets, is known to be related, in part, to their birth weight since below a certain birth weight threshold, mortality rates increase dramatically. Hence agents that increase birth weight by, for instance, promoting foetal growth, reducing or overcoming intrauterine growth retardation or normalising intrauterine growth and/or prolonging or normalising of threatened gestation periods, will tend to reduce the mortality of young animals. Further, agents which promote the growth of oocytes, zygotes, blastocysts or embryos or increase the rate of survival of embryos or foetuses will tend to increase the chances of a viable pregnancy occurring and the number of offspring per pregnancy. Establishing viable pregnancy in dairy cattle is especially important since pregnancy is a prerequisite for lactation to occur. The fertility of dairy cattle has been declining for some time, at the rate of about 1% per annum.

Such agents as described above would be expected to also have obvious applications in companion animals such as cats, dogs and horses, and in human health. Miscarriage and pre-term labour account for significant foetal loss in pregnancy and low birthweight and associated conditions contribute to significant perinatal morbidity and mortality. Also there is increasing evidence that low birth weight in relation to gestational age not only increases the immediate danger to the foetus, but also the incidence of cardiovascular disease, such as carotid stenosis, in later life. Hence agents which promote the growth of oocytes, zygotes, blastocysts, embryos or foetuses, increase the rate of survival of embryos or foetuses or increase the birth weight of a progeny would be useful in the management certain problems in human reproduction.

DETAILED DESCRIPTION OF THE INVENTION

Figure 1:
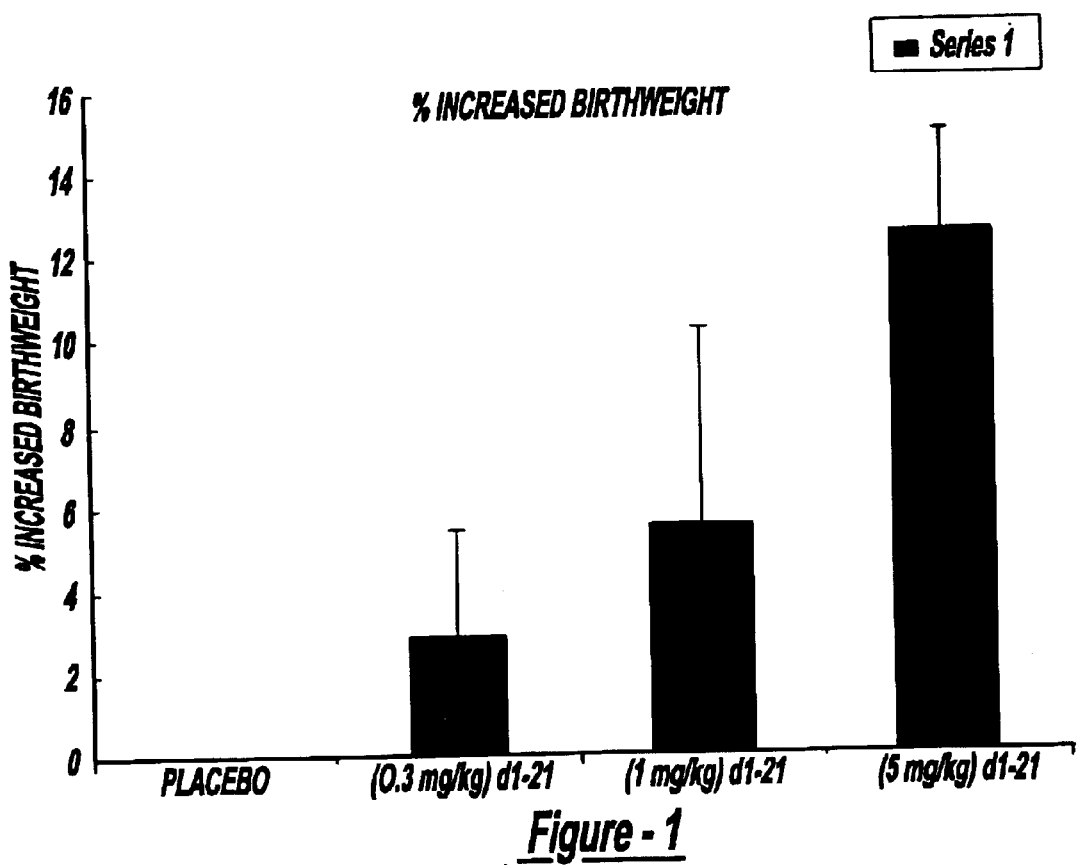
FIG. 1. 3-ethyl-5-(5-(4-ethylpiperazin-1-ylsulphonyl)-2-n-propoxyphenyl)-2-(pyridin-2-yl)methyl-2,6-dihydro-7H-pyrazolo(4,3-d)pyrimidin-7-one administered throughout gestation (days 1-21) increases birthweights of rat puts.

It is an object of the present invention to provide substances which will have utility in increasing fecundity in mammals, including humans, by one or more of the following means: (a) by promoting the growth of an oocyte, zygote, blastocyst, embryo and/or foetus; (b) by increasing the rate or probability of survival rate of an embryo and/or foetus; and (c) by increasing the birth weight of a progeny.

International patent application WO-A-94/28902 discloses that compounds which are inhibitors of the cGMP PDE V enzyme are potent and effective compounds for the treatment of male erectile dysfunction (MED, impotence) and for female sexual disorders. This discovery led to the development of the compound sildenafil (5-[2-ethoxy-5-(4-methyl-1-piperazinylsulphonyl)phenyl]-1-methyl-3-n-propyl-1,6-dihydro-7H-pyrazolo[4,3-d]pyrimidin-7-one) (VIAGRA TM) which has proved to be outstandingly successful as the first orally effective treatment for MED.

Sometimes cGMP PDE V is referred to as PDE V or PDE5. These terms are used interchangeably herein.

It has been reported that sildenafil may be effective for improving uterine artery blood flow and endometrial development in patients undergoing in vitro fertilisation (IVF) with prior poor endometrial response (Hum. Reprod., 2000, 15(4), 806-809).

We have now found that cyclic guanosine 3', 5'-monophosphate phosphodiesterase type five (cGMP PDE V) inhibitors have utility in increasing fecundity in mammals by one or more of (a) promoting the growth of an oocyte, zygote, blastocyst, embryo and/or foetus, (b) increasing the rate or probability of survival of an embryo and/or foetus and (c) increasing the birth weight of a progeny. It may be that the increased fecundity is provided via improved uteroplacental blood flow or prolongation of gestation through relaxation of the uterine smooth muscle or, more likely, a combination of these effects. Our invention however is not limited by such mechanisms of action.

The present invention therefore provides the use of a cyclic guanosine 3',5'-monophosphate phosphodiesterase type five (cGMP PDE V) inhibitor in the manufacture of a medicament for increasing fecundity in a mammal by one or more of (a) promoting the growth of an oocyte, zygote, blastocyst, embryo and/or foetus; (b) increasing the rate or probability of survival of an embryo and/or foetus and (c) increasing the birth weight of a progeny; and a method of treatment which comprises administering a therapeutically effective amount of a cyclic guanosine 3', 5'-monophosphate phosphodiesterase type five (cGMP PDE V) inhibitor, to a female mammal, in order to increase fecundity by one or more of (a) promoting the growth of an oocyte, zygote, blastocyst, embryo and/or foetus, (b) increasing the rate or probability of survival of an embryo and/or foetus and (c) increasing the birth weight of a progeny.

The present invention has potential utility in all mammalian species including human beings. The present invention is potentially particularly useful in human beings, cats, dogs, horses, cattle (including dairy cattle and beef cattle), pigs, sheep and horses. The present invention is potentially most useful in the husbandry of cattle and pigs and in the treatment of human beings.

The present invention has potential utility in all female human beings including fertile, sub-fertile and certain infertile female human beings, those undergoing in vitro fertilisation (IVF) and those not undergoing IVF and both those with a normal endometrial response and those with a poor endometrial response. It potentially has particular utility in those female human beings who have an increased risk of suffering a miscarriage (e.g. those female human beings who have suffered a previous miscarriage or who have undergone amniocentesis) and in older female human beings (e.g. for example those over 35 years of age).

The invention described herein has the potential to improve the endometrial response to exogenous or endogenous stimulus including hormonal stimulus.

The term 'fecundity' means the ability to produce progenies, especially healthy progenies and especially in abundance.

The present invention has the potential to increase fecundity during all the stages of the reproductive process, from ovulation until parturition and references to oocyte, zygote, blastocyst, embryo and foetus should be construed as covering the development of a progeny over this entire period. Thus, in a normal pregnancy, an oocyte will be fertilised and develop progressively into a zygote, blastocyst, embryo and foetus. The foetus will subsequently be born as a neonate.

As explained above, the invention also has consequences for the growth and survival rate of a neonate which, in part, are related to birth weight. The compounds of the invention have the potential to increase the survival rate and growth rate of a neonate, as well as improve the health of the neonate later in its life.

Reproductive performance in the cow is a major factor in the economic success of dairy producers and beef reproduction units. The calving interval is the major parameter to assess bovine reproductive efficiency. In general, a calving interval of approximately 1 year is considered economically optimal for dairy cows. In order to achieve such outcomes, a post partum cow must conceive within 85 days following parturition, while maintaining peak lactational performance. Based on USDA production figures for 1997, the period from parturition to conception was reported to be 130–140 days, which costs the producer $155 per cow per year. It is accepted generally that the decrease in bovine pregnancy is correlated genetically with milk yields. Thus, by selecting cattle exclusively for milk yield, farmers have unknowingly selected against fertility. As a consequence rates of embryo loss are expected to increase further. The use of a PDE V inhibitor in the manner described herein would be expected to reduce the rate of embryo loss and therefore lead to an increase in milk productivity.

The PDE V inhibitors, useful in conjunction with the present invention ("the substances") will usually be administered during the period from ovulation to parturition, either for the whole of or part of that period, though there may be circumstances when administration at other times is appropriate (e.g. prior to ovulation when the time of ovulation is unknown). In particular, in pregnant female humans, the substances will be preferably administered during the first 23 weeks of pregnancy in order to help prevent miscarriage and after 20 weeks in order to help prevent pre-term labour. In this context, pregnancy is taken to start at the date of the last menstrual period.

In cattle, the substances will preferably be administered during the period from day −3 (i.e. 3 days before impregnation) to day 15 of pregnancy.

In pigs, the substances will preferably be administered during the period from day 30, more preferably from day 60, of pregnancy until parturition.

Further aspects of the invention are mentioned in the claims.

Suitable cGMP PDE5 inhibitors for the use according to the present invention include: the pyrazolo [4,3-d] pyrimidin-7-ones disclosed in EP-A-0463756; the pyrazolo [4,3-d]pyrimidin-7-ones disclosed in EP-A-0526004; the pyrazolo [4,3-d]pyrimidin-7-ones disclosed in published international patent application WO 93/06104; the isomeric pyrazolo [3,4-d]pyrimidin-4-ones disclosed in published international patent application WO 93/07149; the quinazolin-4-ones disclosed in published international patent application WO 93/12095; the pyrido [3,2-d] pyrimidin-4-ones disclosed in published international patent application WO 94/05661; the purin-6-ones disclosed in published international patent application WO 94/00453; the pyrazolo [4,3-d]pyrimidin-7-ones disclosed in published international patent application WO 98/49166; the pyrazolo [4,3-d]pyrimidin-7-ones disclosed in published international patent application WO 99/54333; the pyrazolo [4,3-d] pyrimidin-4-ones disclosed in EP-A-0995751; the pyrazolo [4,3-d]pyrimidin-7-ones disclosed in published international patent application WO 00/24745; the pyrazolo [4,3-d] pyrimidin-4-ones disclosed in EP-A-0995750; the compounds disclosed in published international application WO95/19978; the compounds disclosed in published international application WO 99/24433 and the compounds disclosed in published international application WO 93/07124; the pyrazolo [4,3-d]pyrimidin-7-ones disclosed in published international application WO 01/27112; the pyrazolo [4,3-d]pyrimidin-7-ones disclosed in published international application WO 01/27113; the compounds disclosed in EP-A-1092718; and the compounds disclosed in EP-A-1092719. Preferred type V phosphodiesterase inhibitors for the use according to the present invention include: 5-[2-ethoxy-5-(4-methyl-1-piperazinylsulphonyl)phenyl]-1-methyl-3-n-propyl-1,6-dihydro-7H-pyrazolo[4,3-d] pyrimidin-7-one (sildenafil) also known as 1-[[3-(6,7-dihydro-1-methyl-7-oxo-3-propyl-1H-pyrazolo[4,3-d] pyrimidin-5-yl)-4-ethoxyphenyl]sulphonyl]-4-methylpiperazine (see EP-A-0463756);

5-(2-ethoxy-5-morpholinoacetylphenyl)-1-methyl-3-n-propyl-1,6-dihydro-7H-pyrazolo[4,3-d]pyrimidin-7-one (see EP-A-0526004); 3-ethyl-5-[5-(4-ethylpiperazin-1-ylsulphonyl)-2-n-propoxyphenyl]-2-(pyridin-2-yl) methyl-2,6-dihydro-7H-pyrazolo[4,3-d]pyrimidin-7-one (see WO98/49166); 3-ethyl-5-[5-(4-ethylpiperazin-1-ylsulphonyl)-2-(2-methoxyethoxy)pyridin-3-yl]-2-(pyridin-2-yl)methyl-2,6-dihydro-7H-pyrazolo[4,3-d] pyrimidin-7-one (see WO99/54333);

(+)-3-ethyl-5-[5-(4-ethylpiperazin-1-ylsulphonyl)-2-(2-methoxy-1(R)-methylethoxy)pyridin-3-yl]-2methyl-2,6-dihydro-7H-pyrazolo[4,3-d]pyrimidin-7-one, also known as 3-ethyl-5-{5-[4-ethylpiperazin-1-ylsulphonyl]-2-([(1R)-2-methoxy-1-methylethyl]oxy)pyridin-3-yl}-2- methyl-2,6-dihydro-7H-pyrazol o[4,3-d] pyrimidin-7-one (see WO99/54333);

5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, also known as 1-{6-ethoxy-5-[3-ethyl-6,7-dihydro-2-(2-methoxyethyl)-7-oxo-2H-pyrazolo[4,3-d]pyrimidin-5-yl]-3-pyridylsulphonyl}-4-ethylpiperazine (see WO 01/27113, Example 8); 5-[2-iso-Butoxy-5-(4-ethylpiperazin-1-ylsulphonyl)pyridin-3-yl]-3-ethyl-2-(1-methylpiperidin-4-yl)-2,6-dihydro-7H-pyrazolo[4,3-d]pyrimidin-7-one (see WO 01/27113, Example 15);

5-[2-Ethoxy-5-(4-ethylpiperazin-1-ylsulphonyl)pyridin-3-yl]-3-ethyl-2-phenyl-2,6-dihydro-7H-pyrazolo[4,3-d]pyrimidin-7-one (see WO 01/27113, Example 66); 5-(5-Acetyl-2-propoxy-3-pyridinyl)-3-ethyl-2-(1-isopropyl-3-azetidinyl)-2,6-dihydro-7H-pyrazolo[4,3-d]pyrimidin-7-one (see WO 01/27112, Example 124);

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (see WO 01/27112, Example 132);

(6R, 12aR)-2,3,6,7,12,12a-hexahydro-2-methyl-6-(3,4-methylenedioxyphenyl)-pyrazino[2',1':6,1]pyrido[3,4-b]indole-1,4-dione (IC-351), i.e. the compound of examples 78 and 95 of published international application WO95/19978, as well as the compound of examples 1, 3, 7 and 8; 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil) also known as 1-[[3-(3,4-dihydro-5-methyl-4-oxo-7-propylimidazo[5,1-f]-as-triazin-2-yl)-4-ethoxyphenyl]sulphonyl]-4-ethylpiperazine, i.e. the compound of examples 20, 19, 337 and 336 of published international application WO99/24433; and the compound of example 11 of published international application WO93/07124 (EISAI); and compounds 3 and 14 from Rotella D P, J. Med. Chem., 2000, 43, 1257.

Still other type cGMP PDE5 inhibitors useful in conjunction with the present invention include:4-bromo-5-(pyridylmethylamino)-6-[3-(4-chlorophenyl)-propoxy]-3(2H)pyridazinone; 1-[4-[(1,3-benzodioxol-5-ylmethyl)amino]-6-chloro-2-quinozolinyl]-4-piperidine-carboxylic acid, monosodium salt; (+)-cis-5,6a,7,9,9,9a-hexahydro-2-[4-(trifluoromethyl)-phenylmethyl-5-methyl-cyclopent-4,5]imidazo[2,1-b]purin-4(3H)one; furazlocillin; cis-2-hexyl-5-methyl-3,4,5,6a,7,8,9,9a-octahydrocyclopent[4,5]-imidazo[2,1-b]purin-4-one; 3-acetyl-1-(2-chlorobenzyl)-2-propylindole-6-carboxylate; 3-acetyl-1-(2-chlorobenzyl)-2-propylindole-6-carboxylate; 4-bromo-5-(3-pyridylmethylamino)-6-(3-(4-chlorophenyl) propoxy)-3-(2H)pyridazinone; I-methyl-5(5-morpholinoacetyl-2-n-propoxyphenyl)-3-n-propyl-1,6-dihydro-7H-pyrazolo(4,3-d)pyrimidin-7-one; 1-[4-[(1,3-benzodioxol-5-ylmethyl)arnino]-6-chloro-2-quinazolinyl]-4-piperidinecarboxylic acid, monosodium salt; Pharmaprojects No. 4516 (Glaxo Wellcome); Pharmaprojects No. 5051 (Bayer); Pharmaprojects No. 5064 (Kyowa Hakko; see WO 96/26940); Pharmaprojects No. 5069 (Schering Plough); GF-196960 (Glaxo Wellcome); E-8010 and E-4010 (Eisai); Bay-38-3045 & 38-9456 (Bayer) and Sch-51866.

The suitability of any particular cGMP PDE5 inhibitor can be readily determined by evaluation of its potency and selectivity using literature methods followed by evaluation of its toxicity, absorption, metabolism, pharmacokinetics, etc in accordance with standard pharmaceutical practice.

Preferably, the cGMP PDE5 inhibitors have an IC50 at less than 100 nanomolar, more preferably, at less than 50 nanomolar, more preferably still at less than 10 nanomolar.

IC50 values for the cGMP PDE5 inhibitors may be determined using the PDE5 assay in the Test Methods Section hereinafter.

Preferably the cGMP PDE5 inhibitors used in the pharmaceutical combinations according to the present invention are selective for the PDE5 enzyme. Preferably they have a selectivity of PDE5 over PDE3 of greater than 100 more preferably greater than 300. More preferably the PDE5 has a selectivity over both PDE3 and PDE4 of greater than 100, more preferably greater than 300.

Selectivity ratios may readily be determined by the skilled person. IC50 values for the PDE3 and PDE4 enzyme may be determined using established literature methodology, see S A Ballard et al, Journal of Urology, 1998, vol. 159, pages 2164–2171 and as detailed herein after.

It is to be understood that the contents of the above published patent applications, and in particular the general formulae and exemplified compounds therein are incorporated herein in their entirety by reference thereto.

The terms "pharmaceutical" and "pharmaceutically acceptable" as used herein in relation to excipients, diluents, carriers, salts, solvates, etc. includes "veterinary" and "veterinarily acceptable" excipients, diluents, carriers, salts, solvates, etc.

The PDE V inhibitors, their salts and solvates, according to the invention, can be administered alone but will generally be administered in admixture with a suitable pharmaceutical excipient, diluent or carrier selected with regard to the intended route of administration and standard pharmaceutical or veterinary practice. They may be administered in the form of a non-toxic organic or inorganic acid or base addition salt, and/or solvates thereof, as appropriate to the particular PDE V inhibitor.

Specific methods by which the PDE5 inhibitors, their pharmaceutically acceptable salts, and pharmaceutically acceptable solvates of either entity, when used in accordance with the invention, may be administered for veterinary use include oral administration by capsule, bolus, tablet or drench, topical administration as an ointment, pour-on, dip, spray, mousse, shampoo, collar or powder formulation, or, alternatively, they can be administered by injection (e.g. subcutaneously, intramuscularly or intravenously), or as an implant. Such formulations may be prepared in a conventional manner in accordance with standard veterinary practice.

Alternatively, in veterinary use, the PDE5 inhibitors, their pharmaceutically acceptable salts, and pharmaceutically acceptable solvates of either entity, when used in accordance with the invention, may be administered with an animal feedstuff and for this purpose a concentrated feed additive or premix may be prepared for mixing with the normal animal feed.

The PDE5 inhibitors, their pharmaceutically acceptable salts, and pharmaceutically acceptable solvates of either entity, when used in accordance with the invention, can be administered orally, buccally or sublingually in the form of tablets, capsules (including soft gel capsules), ovules, elixirs, solutions or suspensions, which may contain flavouring or colouring agents, for immediate-, delayed-, modified-, or controlled-release such as sustained-, dual-, or pulsatile delivery applications. The PDE5 inhibitors, their pharmaceutically acceptable salts, and pharmaceutically acceptable solvates of either entity, when used in accordance with the invention, may also be administered via fast dispersing or fast dissolving dosages forms or in the form of a high energy dispersion or as coated particles. Suitable pharmaceutical formulations of the PDE5 inhibitors, their pharmaceutically acceptable salts, and pharmaceutically acceptable solvates of either entity, when used in accordance with the invention, may be in coated or uncoated form as desired.

Such tablets may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethyl cellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

Modified release and pulsatile release dosage forms may contain excipients such as those detailed for immediate release dosage forms together with additional excipients that act as release rate modifiers, these being coated on and/or included in the body of the device. Release rate modifiers include, but are not exclusively limited to, hydroxypropylmethyl cellulose, methyl cellulose, sodium carboxymethylcellulose, ethyl cellulose, cellulose acetate, polyethylene oxide, Xanthan gum, Carbomer, ammonio methacrylate copolymer, hydrogenated castor oil, carnauba wax, paraffin wax, cellulose acetate phthalate, hydroxypropylmethyl cellulose phthalate, methacrylic acid copolymer and mixtures thereof. Modified release and pulsatile release dosage forms may contain one or a combination of release rate modifying excipients. Release rate modifying excipients maybe present both within the dosage form i.e. within the matrix, and/or on the dosage form i.e. upon the surface or coating.

Fast dispersing or dissolving dosage formulations (FDDFs) may contain the following ingredients: aspartame, acesulfame potassium, citric acid, croscarmellose sodium, crospovidone, diascorbic acid, ethyl acrylate, ethyl cellulose, gelatin, hydroxypropylmethyl cellulose, magnesium stearate, mannitol, methyl methacrylate, mint flavouring, polyethylene glycol, fumed silica, silicon dioxide, sodium starch glycolate, sodium stearyl fumarate, sorbitol, xylitol. The terms dispersing or dissolving as used herein to describe FDDFs are dependent upon the solubility of the drug substance used i.e. where the drug substance is insoluble a fast dispersing dosage form can be prepared and where the drug substance is soluble a fast dissolving dosage form can be prepared.

The PDE5 inhibitors, their pharmaceutically acceptable salts, and pharmaceutically acceptable solvates of either entity, when used in accordance with the invention, can also be administered parenterally, for example, intravenously, intra-arterially, intraperitoneally, intrathecally, intraventricularly, intraurethrally intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

For oral and parenteral administration to human patients, the daily dosage level of the PDE5 inhibitors, their pharmaceutically acceptable salts, and pharmaceutically acceptable solvates of either entity, when used in accordance with the invention, will usually be from 10 to 500 mg (in single or divided doses).

Thus, for example, tablets or capsules of the PDE5 inhibitors, their pharmaceutically acceptable salts, and pharmaceutically acceptable solvates of either entity, when used in accordance with the invention, may contain from 5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention. The skilled person will also appreciate that, in the treatment of certain conditions the PDE5 inhibitors, their pharmaceutically acceptable salts, and pharmaceutically acceptable solvates of either entity, when used in accordance with the invention, may be taken as a single dose on an "as required" basis (i.e. as needed or desired).

Example Tablet Formulation

In general a tablet formulation could typically contain between about 0.01 mg and 500 mg of a PDE5 inhibitor, or a pharmaceutically acceptable salt, or pharmaceutically acceptable solvate of either entity, when used in accordance with the invention, whilst tablet fill weights may range from 50 mg to 1000 mg. An example formulation for a 10 mg tablet is illustrated:

| Ingredient | % w/w |
| --- | --- |
| Free acid, Free base or Salt of Compound | 10.000* |
| Lactose | 64.125 |
| Starch | 21.375 |
| Croscarmellose Sodium | 3.000 |
| Magnesium Stearate | 1.500 |

*This quantity is typically adjusted in accordance with drug activity.

The tablets are manufactured by a standard process, for example, direct compression or a wet or dry granulation process. The tablet cores may be coated with appropriate overcoats.

The PDE5 inhibitors, their pharmaceutically acceptable salts, and pharmaceutically acceptable solvates of either entity, when used in accordance with the invention, can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark] or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" contains from 1 to 50 mg of a PDE5 inhibitor, or a pharmaceutically acceptable salt, or pharmaceutically acceptable solvate of either entity, when used in accordance with the invention, for delivery to the patient. The overall daily dose with an aerosol will be in the range of from 1 to 50 mg which may be administered in a single dose or, more usually, in divided doses throughout the day.

The PDE5 inhibitors, their pharmaceutically acceptable salts, and pharmaceutically acceptable solvates of either entity, when used in accordance with the invention, may also be formulated for delivery via an atomiser. Formulations for atomiser devices may contain the following ingredients as solubilisers, emulsifiers or suspending agents: water, ethanol, glycerol, propylene glycol, low molecular weight polyethylene glycols, sodium chloride, fluorocarbons, polyethylene glycol ethers, sorbitan trioleate, oleic acid.

Alternatively, the PDE5 inhibitors, their pharmaceutically acceptable salts, and pharmaceutically acceptable solvates of either entity, when used in accordance with the invention, can be administered in the form of a suppository or pessary, or they may be applied topically in the form of a gel, hydrogel, lotion, solution, cream, ointment or dusting powder. The PDE5 inhibitors, their pharmaceutically acceptable salts, and pharmaceutically acceptable solvates of either entity, when used in accordance with the invention, may also be dermally administered. The PDE5 inhibitors, their pharmaceutically acceptable salts, and pharmaceutically acceptable solvates of either entity, when used in accordance with the invention, may also be transdermally administered, for example, by the use of a skin patch. They may also be administered by the ocular, pulmonary or rectal routes.

For ophthalmic use, the PDE5 inhibitors, their pharmaceutically acceptable salts, and pharmaceutically acceptable solvates of either entity, when used in accordance with the invention, can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the PDE5 inhibitors, their pharmaceutically acceptable salts, and pharmaceutically acceptable solvates of either entity, when used in accordance with the invention, can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The PDE5 inhibitors, their pharmaceutically acceptable salts, and pharmaceutically acceptable solvates of either entity, when used in accordance with the invention, may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

Generally, in humans, oral administration of the PDE5 inhibitors, their pharmaceutically acceptable salts, and pharmaceutically acceptable solvates of either entity, when used in accordance with the invention, is the preferred route. A preferred oral dosing regimen is from 25 to 250 mg of compound when required. In circumstances where the recipient suffers from a swallowing disorder or from impairment of drug absorption after oral administration, the drug may be administered parenterally, sublingually or buccally.

For veterinary use, PDE5 inhibitors, their veterinarily acceptable salts, and veterinaraly acceptable solvates of either entity, when used in accordance with the invention, or pro-drug thereof, is administered as a suitably acceptable formulation in accordance with normal veterinary practice and the veterinary surgeon or formulator will determine the dosing regimen and route of administration which will be most appropriate for a particular animal.

Generally, in non-human animals, oral administration (for instance in feed) or vaginal administration are preferred. Oral administration is particularly preferred in pigs, and vaginal administration (for example of a PDE V inhibitor in a suspension, e.g. with cellulose) is particularly preferred in cattle.

The PDE5 inhibitors, their pharmaceutically or veterinarilly acceptable salts, and pharmaceutically or veterinarilly acceptable solvates of either entity, when used in accordance with the invention, may be administered either alone or in combination with one or more therapeutic agents, e.g. an agent used in the treatment or prophylaxis of disease or in the reduction or suppression of symptoms.

The following formulation examples are illustrative only and are not intended to limit the scope of the invention. Active ingredient means a compound of the invention.

Formulation 1

A tablet is prepared using the following ingredients:

|  | Weight (mg) |
| --- | --- |
| Active ingredient | 250 |
| Cellulose, microcrystalline | 400 |
| Silicon dioxide, fumed | 10 |
| Stearic acid | 5 |
| Total | 665 | the components are blended and compressed to form tablets each weighing 665 mg.

Formulation 2

An intravenous formulation may be prepared by combining active ingredient (100 mg) with isotonic saline (1000 ml).

Formulations of 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one Formulations of 3-ethyl-5-[5-(4-ethylpiperazin-1-ylsulphonyl)-2-n-propoxyphenyl]-2-(pyridin-2-yl)methyl-2, 6-dihydro-7H-pyrazolo[4,3-d]pyrimidin-7-one at up to 5 mg/ml were made with the following solvent:

glycerol formal:Tween 80:Benzyl alcohol (24:17:1.5)-3 parts; water-1 part

EXAMPLES

The following experiments demonstrate the activity of cyclic guanosine 3',5'-monophosphate phosphodiesterase type five (cGMP PDE V) inhibitors in the claimed uses.

Experiment 1

Female mice of the CBA strain (obtained from Charles River, UK) were crossed with male mice of the DBA strain (obtained from Charles River, UK) and treated i.p. with 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one at the rate of either 1 mg/kg or 3 mg/kg on days 1 to 8 of gestation. The mice were euthanised on day 12 of gestation and the numbers of viable and non-viable embryos were determined relative to corresponding control mice. The results are set out in Table 1.

Table 1. The effect of daily dosing on days 1-8 with 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one on embryo survival of CBAxDBA mice.

| Treatment | % Embryo Survival |
| --- | --- |
| Control | 51 |
| 1 mg/kg test compound | 90 |
| 3 mg/kg test compound | 84 |

Administration of 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one on days 1 to 8 of gestation improves significantly the rate of embryo survival and the maintenance of pregnancy in CBAxDBA mice.

Experiment 2

Female mice of the CBA strain (obtained from Charles River, UK) were crossed with male mice of the DBA strain (obtained from Charles River, UK) and treated i.p. with 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one at the rate of 1 mg/kg on days 1 to 4 or 4 to 8 of gestation. The mice were euthanised on day 12 of gestation and the numbers of viable and non-viable embryos were determined relative to corresponding control mice. The results are set out in Table 2.

Table 2. The effect of daily dosing on days 1-4 or 4-8 of gestation with 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one on embryo survival of CBAxDBA mice.

| Treatment | % Embryo Survival |
| --- | --- |
| Control | 54 |
| 1 mg/kg test compound days 1–4 | 81 |
| 1 mg/kg test compound days 4–8 | 70 |

The administration of 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one on days 1-4 or 4-8 improved the rate of embryo survival in both cases, which suggests it could be used in the treatment of females with a history of single or recurrent or habitual spontaneous abortion or preterm birth, or to prevent such conditions.

Experiment 3

To evaluate the effects of cGMP PDE V inhibition on embryonic and foetal growth, 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one was administered s.c. daily in an aqueous micelle formulation at the rate of 0.3, 1 and 5 mg/kg to pregnant rats. The results are illustrated in FIG. 1.

It is evident that daily administration of 3-ethyl-5-[5-(4-ethylpiperazin-1ylsulphonyl)-2-n-propoxyphenyl]-2-(pyridin-2-yl)methyl-2,6-dihydro-7H-pyrazolo[4,3-d]pyrimidin-7-one, and by extrapolation, other effective PDE V inhibitors, to pregnant rats, and by extrapolation other mammals, promotes embryonic and/or foetal growth and consequently increases birthweight.

A comparative experiment using a similar protocol was carried out using (A) 3-ethyl-5-[5-(4-ethylpiperazin-1-ylsulphonyl)-2-n-propoxyphenyl]-2-(pyridin-2-yl)methyl-2,6-dihydro-7H-pyrazolo[4,3-d]pyrimidin-7-one and the Lilly-ICOS PDE V inhibitor (B) CILIAS/IC-351. The compounds were administered throughout gestation subcutaneously to pregnant rats (n=10) and the birthweights of their corresponding rat pups were measured. The results are shown in the table below.

| Compound (mg/kg) | % increase | sem* |
| --- | --- | --- |
| control (0) | 0 | 0.25 |
| A (0.3) | 2 | 0.5 |
| A (1) | 6 | 0.6 |
| A (5) | 10 | 0.25 |
| A (10) | 12 | 0.8 |
| B (0.3) | 0 | 0.28 |
| B (1) | 1 | 0.56 |
| B (5) | 5 | 1.2 |

*standard error of the mean

These results clearly demonstrate that PDE V inhibitors increase the birthweights of the rat pups, and that compound A is more effective than compound B in this test.

Experiment 4

Figure 2:
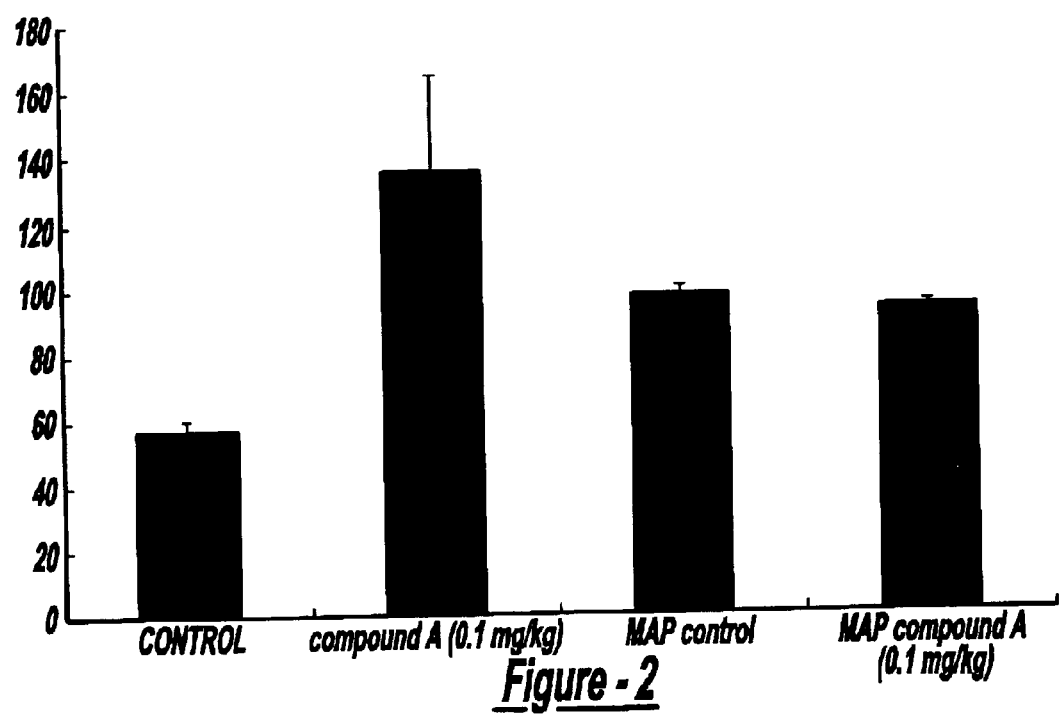
FIG. 2. PDE V inhibition (Compound A) improves significantly uterine blood relative to control animals. No significant effect on mean arterial blood pressure was observed in response to treatment. The Y-axis for the two left hand bars is uterine blood flow (ml/min) and for the two right hand bars is MAP (mmHg).
Figure 3B:
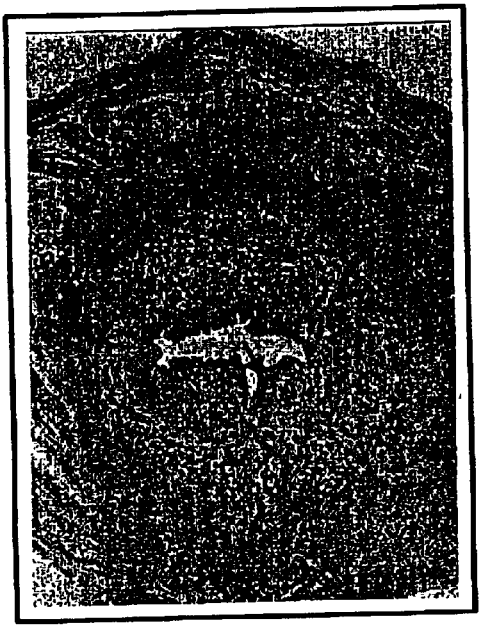
FIG. 3. Cross-section of the uterine horn of control animals, wherein arrows depict endometrial epithelial layer.
Figure 3D:
Figure 3A:
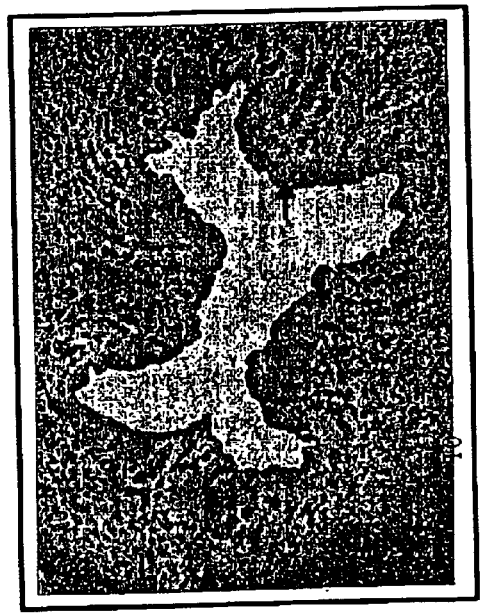
Figure 3C:
Figure 4B:
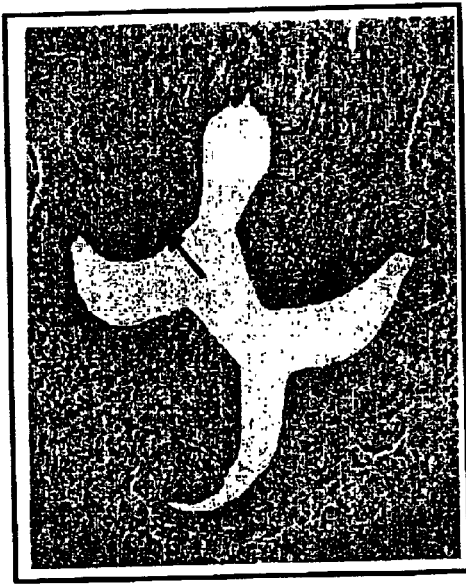
FIG. 4. Cross-section of the uterine horn of animals treated with a PDE V inhibitor (compound A), wherein arrows depict endometrial epithelial layer.
Figure 4D:
Figure 4A:
Figure 4C:
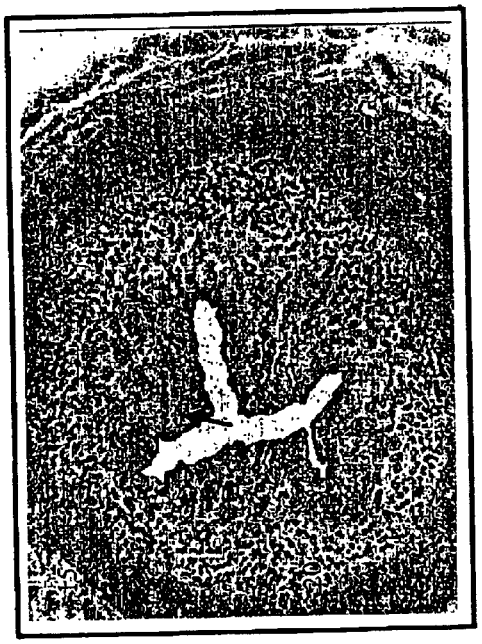
Figure 5:
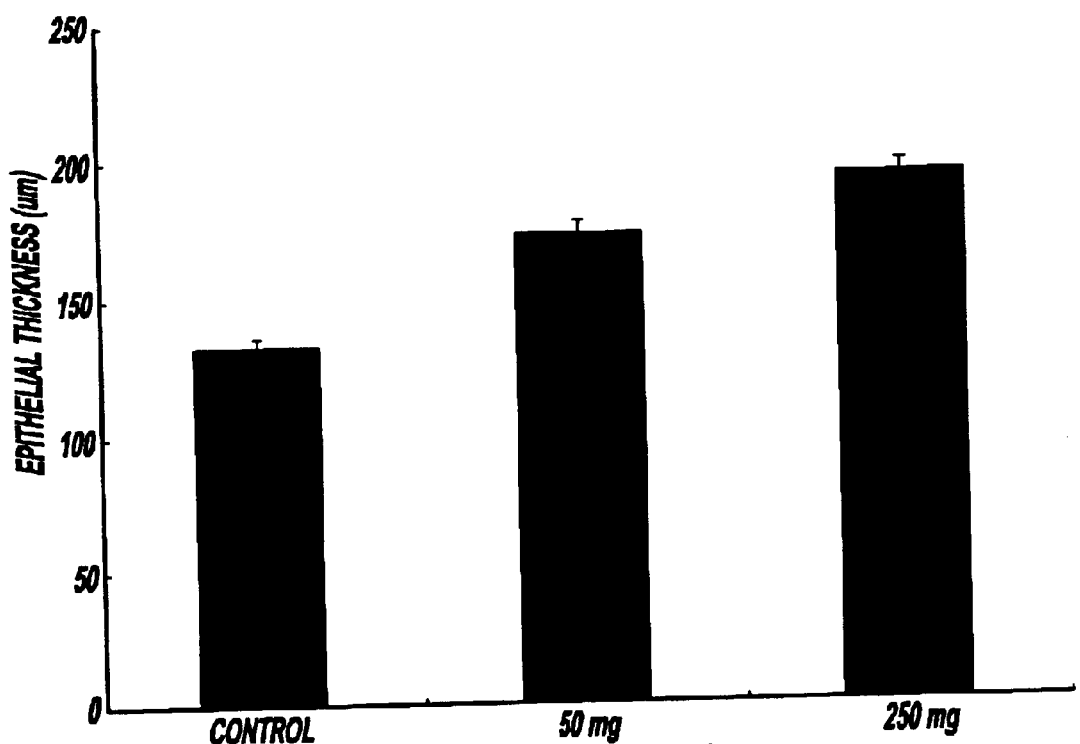
FIG. 5. PDE V inhibitor (compound A) increases endometrial epithelial thickness relative to control animals.

A model of uterine blood flow was established to assess the effects of PDE V inhibition on uterine flow and mean arterial blood pressure (MAP). Mini-pigs weighing approximately 30 kg were modified surgically. As a means of quantifying real time uterine blood flow a Transoinc blood flow probe was placed around either the left or right uterine artery. Catheters were inserted into a external jugular vein and a carotid artery for blood sampling/administration of compound and measurement of mean arterial blood pressure (MAP) respectively. Test compound was administered intravenously either during oestrous or the luteal phase of the reproductive cycle and the effects of PDE V inhibition on uterine blood flow and MAP were measured. The results are shown in FIG. 2. The Y-axis for the two left hand bars is uterine blood flow (ml/min.), and for the two right hand bars is MAP (mmHg).

It was concluded from these experiments that PDE V inhibition augments uterine blood during oestrus (or the time of ovulation). Surprisingly, PDE V inhibition had no effect on uterine blood flow during the luteal phase. It is suggested that oestrogen plays a key role in the actions of PDE V in promoting uterine blood flow.

Experiment 5

Twenty-seven (27) female Friesian cross heifers, approximately 24 months of age were allocated randomly to three treatment groups control, 50 mg and 250 mg of the PDE V inhibitor administered intra-vaginally twice daily.

Oestrous was synchronised using two intramuscular injections of PGF2 alpha (Lutalyse TM ) administered 11 days apart.

The PDE V inhibitor was administered intra-vaginally twice daily from day −3 of oestrus until day 6 of the following oestrus (30 days in total). Blood samples were collected daily, plasma was prepared as soon as possible and stored at −20 DEG C and then analysed for progesterone.

At the completion of the study (ie day 6 of the second oestrous period) the cattle were euthanised and the reproductive tract collected. A cross section of the left and right horns of each uterus was collected and stored in 10% Formalin and then analysed histologically.

Figure 6:
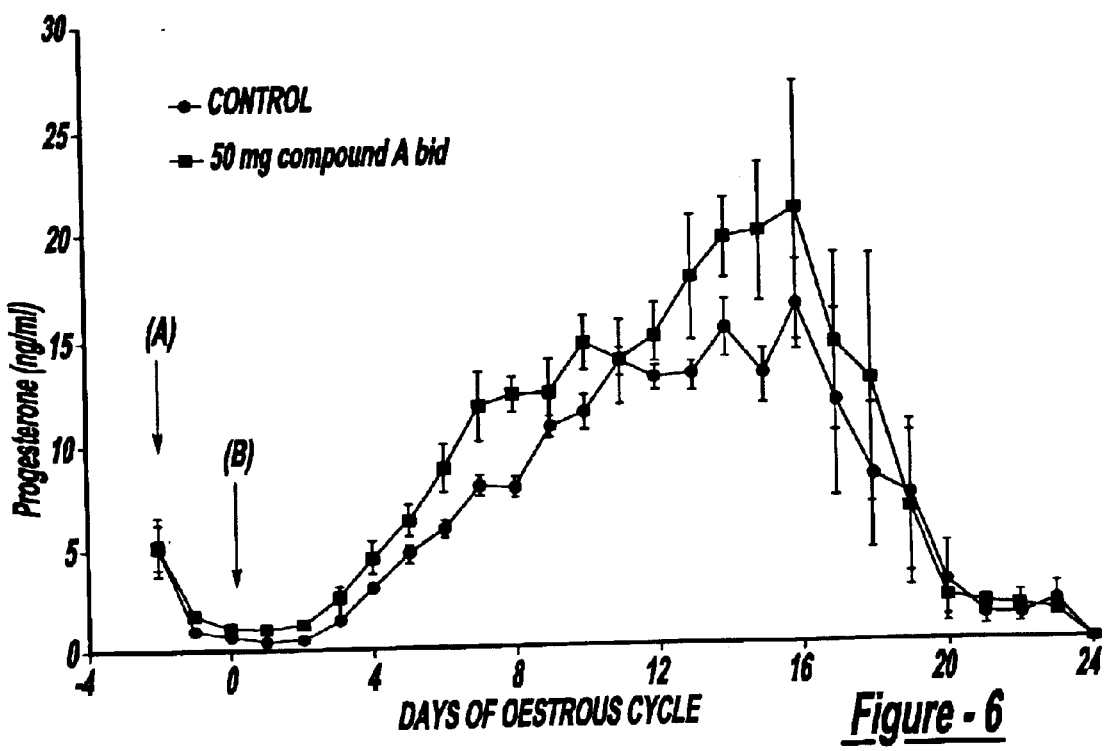
FIG. 6. Concentrations of plasma progesterone in control and PDE V treated animals, wherein (A) indicates start of treatment and (B) indicates oestrus.

It is evident from FIG. 6 that PDE V inhibition enhances significantly progesterone concentrations relative to corresponding control animals. This early rise in progesterone is essential for early ovum quality, embryo growth, foetal development and subsequent maintenance of pregnancy.

It is concluded from the results described above that PDE V inhibition promotes fecundity in mammals. The mechanism(s) by which this is achieved are complex and involve for example early oocyte and embryo growth, uterine and ovarian blood flow, hormonal profiles (for example progesterone) and endometrial growth/function. PDE V inhibition promotes uterine and ovarian blood flow resulting in enhanced nutrient supply to the reproductive organs. This in turn causes an increase in concentrations of progesterone, leading to enhanced oocyte growth/quality, improved endometrial environment, enhanced embryo growth/quality, improved foetal perfusion and subsequent growth.

The results of experiment 5 show that treatment with a PDE V inhibitor leads to increased levels of progesterone. It is proposed herein that PDE V inhibition promotes ovarian blood flow which in turn results in enhanced nutrient supply to the ovary and increased progesterone levels. Thus, according to a further aspect, the present invention additionally provides for the use of PDE V inhibitors for treatment of conditions where a low progesterone level is implicated. Such conditions are commonly referred to as low progesterone disorders. Low as defined herein means a female having progesterone level(s) during the luteal phase of the menstrual cycle which is inferior to the normal luteal level(s) expected in a pre-menopausal female mammal of her age. Examples of low progesterone disorders potentially treatable according to this aspect of the invention include poor endometrial gland function, short luteal phases, short menstrual cycles, pre-menstrual syndromes and recurrent abortion. Suitable cGMP PDE5i's for such treatment are those described hereinbefore and particularly include potent and selective cGMP PDE5i's. Especially preferred for such treatment is sildenafil. Whilst any the chosen PDE5i and sildenafil in particular can be formulated and dosed for the treatment of low progesterone disorders according to any of the means described herein before, oral and intra-vaginal dosing are preferred, intra-vaginal being particularly preferred.

What is claimed is:

1. A method of increasing fecundity in a female mammal by administering a cyclic guanosine 3',5'-monophosphate phosphodiesterase type five (cGMP PDE V) inhibitor to (a) promote the growth of an oocyte, zygote, blastocyst, embryo and/or fetus; (b) increase the rate or probability of survival of an embryo and/or fetus; and (c) increase the birth weight of a progeny.

2. A method of increasing the survival rate or growth of a neonate born from a female mammal by administering a cyclic guanosine 3',5'-monophosphate phosphodiesterase type five (cGMP PDE V) inhibitor to the female mammal.

* * * * *